United States Patent

Roos et al.

[11] Patent Number: 4,521,542
[45] Date of Patent: Jun. 4, 1985

[54] ARYLSULPHONYL HYDRAZONES AS BLOWING AGENTS

[75] Inventors: Ernst Roos, Odenthal; Klaus Kircher, Leverkusen, both of Fed. Rep. of Germany

[73] Assignee: Bayer Aktiengesellschaft, Leverkusen, Fed. Rep. of Germany

[21] Appl. No.: 619,612

[22] Filed: Jun. 11, 1984

[30] Foreign Application Priority Data

Jun. 21, 1983 [DE] Fed. Rep. of Germany ....... 3322320

[51] Int. Cl.³ .................... C08J 9/06; C07C 143/825
[52] U.S. Cl. ...................................... 521/89; 521/121; 521/146; 521/189; 564/81
[58] Field of Search .................... 564/81; 521/89, 121, 521/189, 146

[56] References Cited

U.S. PATENT DOCUMENTS

| | | | |
|---|---|---|---|
| 2,513,826 | 7/1950 | Sprung et al. | 564/81 |
| 2,552,065 | 5/1951 | Schoene | 564/81 |
| 2,626,933 | 1/1953 | Lober et al. | 260/2.5 |
| 2,673,220 | 3/1954 | Hunter | 564/81 |
| 3,888,802 | 6/1975 | Hunter | 564/81 X |
| 3,912,779 | 10/1975 | Tarnow et al. | 260/556 H |
| 3,925,466 | 12/1975 | Hunter | 564/81 X |
| 4,096,100 | 6/1978 | Hunter et al. | 564/81 X |
| 4,164,611 | 8/1979 | Schmidt et al. | 564/81 X |
| 4,327,196 | 4/1982 | West et al. | 524/120 |
| 4,329,499 | 5/1982 | Horstmann et al. | 564/81 |

FOREIGN PATENT DOCUMENTS

| | | | |
|---|---|---|---|
| 2949069 | 6/1981 | Fed. Rep. of Germany | 564/81 |
| 0598301 | 4/1978 | Switzerland | 564/81 |

*Primary Examiner*—Paul F. Shaver
*Attorney, Agent, or Firm*—Connolly and Hutz

[57] ABSTRACT

The use of arylsulphonyl hydrazones corresponding to the following general formula:

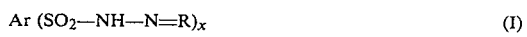

wherein

Ar represents a benzene, naphthalene, diphenyl, diphenyl ether, diphenyl sulphone or diphenylene oxide radical which may be substituted by methyl and/or chlorine;

R represents the radical of an aldehyde or ketone without the carbonyl oxygen atom; and x represents 1 or 2;

as blowing agents for the production of cellular or porous plastics articles.

4 Claims, No Drawings

ARYLSULPHONYL HYDRAZONES AS BLOWING AGENTS

This invention relates to the use of arylsulphonyl hydrazones corresponding to the following general formula:

 (I)

wherein
- Ar represents a benzene, naphthalene, diphenyl, diphenyl ether, diphenyl sulphone or diphenylene oxide radical which may be substituted by methyl and/or chlorine;
- R represents the radical of an aldehyde or ketone without the carbonyl oxygen atom; and
- x represents 1 or 2;

as blowing agents for the production of cellular or porous articles, in particular thermoplastic foams.

It is known to produce foams from thermoplastic materials by working an organic blowing agent into the plastics or by powdering a blowing agent onto a granulated plastics material, which blowing agent decomposes with the evolution of gas at a temperature at which the polymer softens plastically.

Different compounds have been proposed for this purpose (see Angewandte Chemie 64 (1952) pages 65–76).

At present, azodicarbonamide and aromatic sulphohydrazides in particular are used commercially as blowing agents. However, they are not suitable for some plastics. Above all, plastics containing ester groups are easily decomposed by the $NH_2$ groups of these blowing agents, which leads to a deterioration in the mechanical properties of these plastics.

When azodicarbonamide is used, the decomposition gases also contain ammonia which may lead to corrosion of metal moulds and of other parts of the apparatus, and to the production of unpleasant odours. When aromatic sulphohydrazides are used as blowing agents, unpleasant odours may be produced due to sulphur compounds in the decomposition products. Moreover, the decomposition point of aromatic sulphohydrazides in the case of plastics which have to be processed at relatively high temperatures, for example polycarbonates, polyterephthalates and also plastics alloys which contain polyesters of this type, is, however, too low for the formation of a regular foam.

The arylsulphonyl hydrazones according to the present invention which correspond to general formula (I) do not suffer from these disadvantages.

They may be produced by the reaction of arylsulphohydrazides (A) with aldehydes or ketones (B) with the release of water according to the following equation:

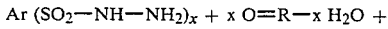

(I)

wherein Ar, R and x are as defined above. R is more especially a $C_1$–$C_8$Alkyl or a $C_6$–$C_{12}$-Arylradical.

For example, the components A and B may be reacted in the presence or absence of solvent and the water which is produced may be removed by distillation under normal or reduced pressure or by azeotropic distillation.

The reaction temperature is generally from 0° to 100° C., preferably from 15° to 80° C. The reactants are generally used in approximately stoichiometric quantities. An excess of one reactant up to about double the stoichiometric quantity is possible.

If the reaction is carried out in a solvent, polar solvents are particularly suitable. The quantity of solvent is calculated so that easily stirrable suspensions of the starting materials are produced.

Examples of suitable starting materials as arylsulphohydrazides include the following: benzene sulphohydrazide, o-, m- and p-toluene sulphohydrazide, p-t-butyl-benzene sulphohydrazide, p-, m-, p-chlorobenzene sulphohydrazide, 5-chloro-2-methyl-benzene sulphohydrazide, 3-chloro-4-methyl-benzene sulphohydrazide, 2-chloro-4-methyl-benzene sulphohydrazide, naphthalene-1-sulphohydrazide, naphthalene-2-sulphohydrazide, diphenyl-4-sulphohydrazide, benzene-1,3-disulphohydrazide, naphthalene-1,4-disulphohydrazide, naphthalene-1,5-disulphohydrazide, naphthalene-2,6-disulphohydrazide, diphenyl-1,4-disulphohydrazide, diphenyl ether-4,4'-disulphohydrazide, ditoluyl ether-disulphohydrazide, diphenyl sulphone-3,3'-disulphohydrazide and diphenylene oxide-4,4'-disulphohydrazide.

Examples of suitable aldehydes and ketones include those which have aliphatic, cycloaliphatic and/or aromatic radicals, in which case the total number of carbon atoms should not exceed 10. The following are mentioned in particular: acetaldehyde, propionaldehyde, n-butyraldehyde, isobutyraldehyde, heptanal, 2-ethylhexanal, tetrahydrobenzaldehyde, hexahydrobenzaldehyde, benzaldehyde, o-, m-, p-toluylaldehyde, acetone, butanone, 2-pentanone, 3-pentanone, 3-methyl-2-butanone, 4-methyl-2-pentanone, 4-heptanone, 5-methyl-3-heptanone, 2,6-dimethyl-4-heptanone, acetophenone, propiophenone, tetralone, cyclohexanone, o-, m-, p-methyl-cyclohexanone and 3,3,5-trimethyl-cyclohexanone.

The reaction of components A and B is preferred in a low-boiling, water miscible alcohol, for example methanol or ethanol, optionally at a temperature of from 15° to 80° C.

Some arylsulphonyl hydrazones are indicated below as examples of the blowing agents according to the present invention:

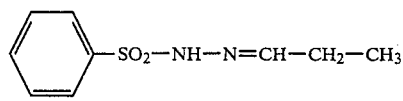

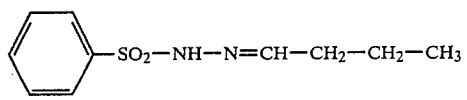
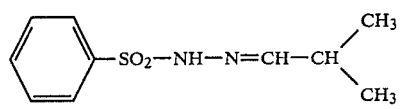
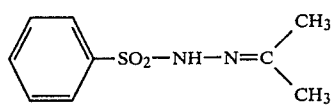
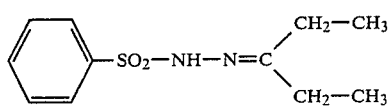
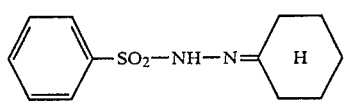
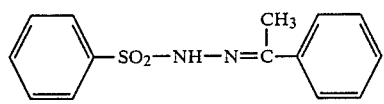
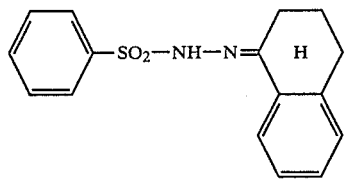
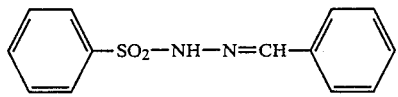
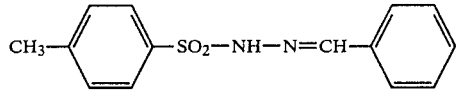
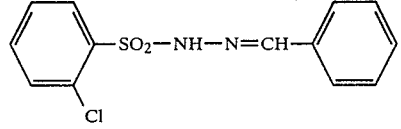
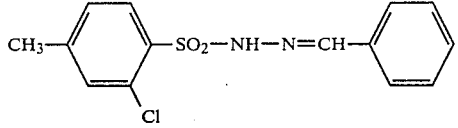
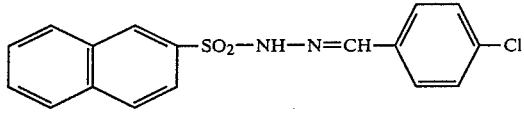

-continued

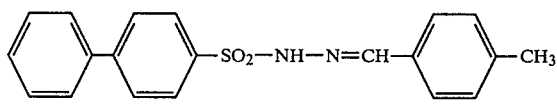

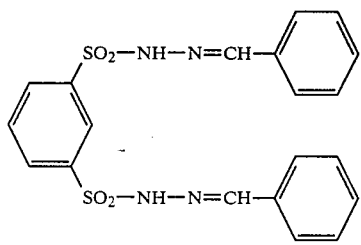

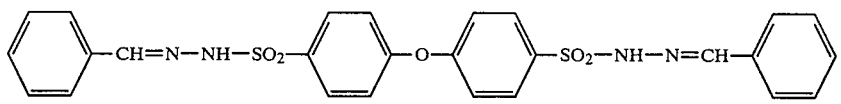

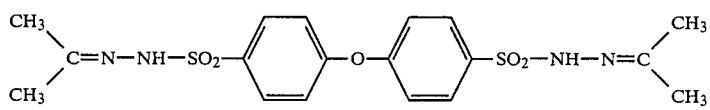

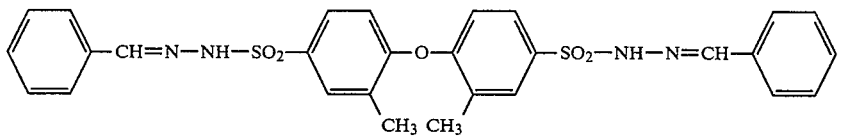

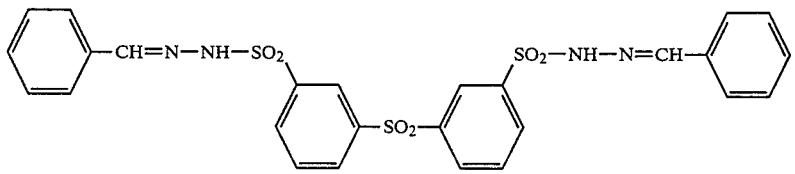

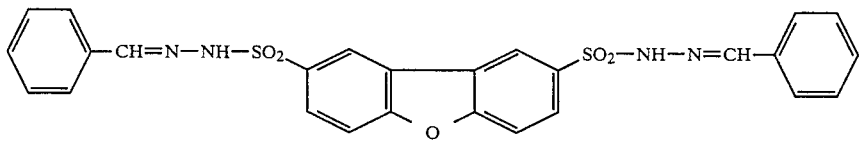

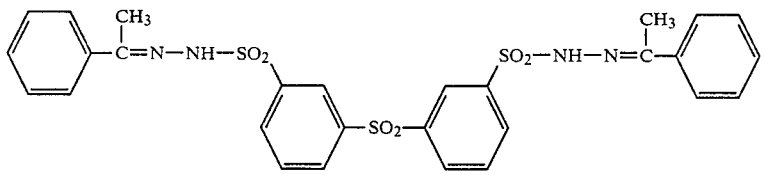

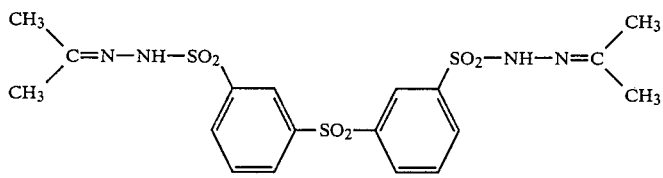

The present arylsulphonyl hydrazones are suitable as blowing agents for thermoplastic polymers, for example vinyl polymers and polycondensates. However, they are preferably used in plastics which contain ester groups, for example polycarbonates and polyesters and in plastics alloys which contain polycarbonates and polyesters. Polycarbonates based on bisphenol A are more preferred as polycarbonates and polyesters based on polybutylene terephthalate are more preferred as polyesters.

The blowing agents to be used according to the present invention may be mixed into the mixtures to be foamed in a conventional manner in an amount of e.g. 0.2 to 1.0 weight percent, for example on mixing rollers, in internal mixers or mixing vessels which are equipped with stirrers. They may be added at the same time as other ingredients of the mixture.

The mixtures may also contain other known auxiliaries, for example fillers, antioxidants, stabilizers, waxes, dyes, pigments, plasticizers, lubricants and peroxides.

EXAMPLES OF THE PRODUCTION OF ARYL-MONOSULPHONYL HYDRAZONES AND ARYL-BIS-SULPHONYL HYDRAZONES

Example 1

N-benzylidene-N'-benzene sulphonyl-hydrazine:

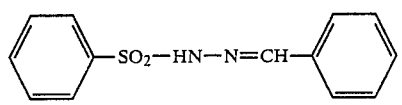

1.72 g (1 mol) of benzene sulphohydrazide in 500 ml of methanol were mixed with 106 g (1 mol) of benzaldehyde at from 20° to 40° C. The mixture was refluxed for 4 hours and, after cooling, the precipitated crystals were suction filtered, washed with methanol and water and dried in a circulating air drying chamber at from 60° to 70° C.

Yield: 222 g=85.3% of the theoretical yield of colourless crystals having a melting point of from 110° to 112° C.

A further crystal fraction having a melting point of from 108° to 110° C. may be obtained from the mother liquor.

Example 2

N,N'-bis-benzylidene-benzene-1,3-disulphonylhydrazine:

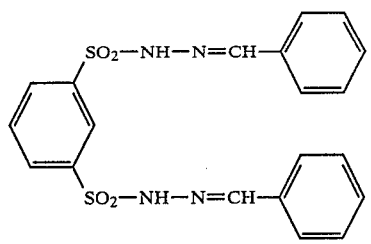

47 g of benzene-1,3-disulphohydrazide, 300 ml of methanol and 37.5 g of benzaldehyde were refluxed for 4 hours. After cooling, the precipitated crystals were suction filtered and dried.

70 g of colourless crystals having a melting point of 182° C. were obtained.

Example 3

N,N'-bis-benzylidene-diphenyl oxide-1,4-disulphonylhydrazine:

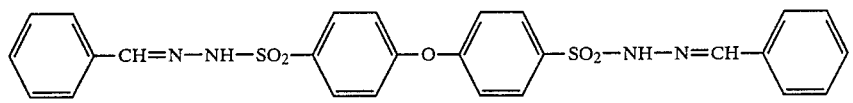

143 g of diphenyl oxide-4,4'-disulphohydrazide, 600 ml of methanol and 85 g of benzaldehyde were refluxed for 4 hours.

After about 300 ml of methanol/water mixture had been distilled off and after cooling, the precipitated crystals were suction filtered and dried.

Yield: 165 g of almost colourless crystals, M.P. 110°–111° C.

Example 4

N,N'-bis-benzylidene-diphenylene oxide-4,4'-disulphonylhydrazine

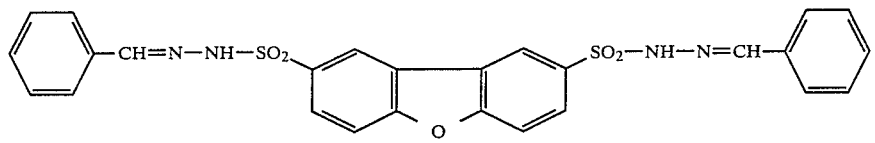

178 g of diphenylene oxide-4,4'-disulphohydrazide, 800 ml of methanol and 106 g of benzaldehyde were refluxed for 4 hours. After cooling to 0° C., the crystal mass was suction filtered and dried.

Yield: 218 g of almost colourless crystals, M.p. 207° C.

EXAMPLE 5

N,N'-bis-benzylidene-2,2'-dimethyl-diphenyl oxide-4,4'-disulphonylhydrazine

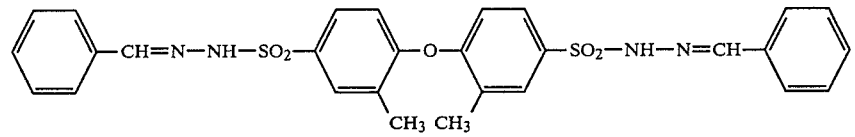

193 g of 2.2'-dimethyl-diphenyloxide-4.4'-disulfohydrazide, 800 ml methanol and 106 g benzaldehyde were stirred for 5 hours at room temperature whereby first resulted a solution and thereafter a crystallinee paste. This paste was suction filtered and dried.

Yield: 265 g of almost colourless crystals, M.p. 172° C.

Example 6

N,N'-bis-benzylidene-diphenylsulfon-3,3'-disulfonylhydrazine

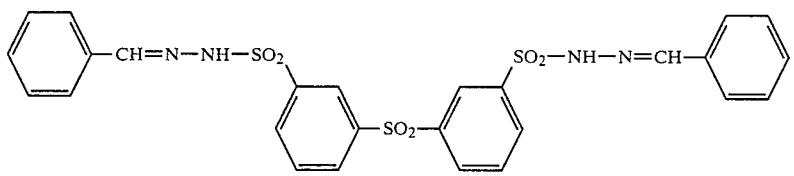

203 g of diphenylsulfon-3,3'-disulfohydrazide, 800 ml methanol and 106 g benzaldehyde were kept boiling for 4 hours under reflux. After cooling the crystalline mass was suction filtered and dried.

Yield: 250 g colourless crystalline powder, M.p. 204° C.

Example 7 (Comparative Experiment)

(a) A bisphenol-A polycarbonate having a melt viscosity of 10 g/10 min (300° C., 1.2 kg) was mixed in a tumbler with 0.35%, by weight, of standard azodicarbonamide ($H_2N$—CO—N=N—CO—$NH_2$) and then injected into mouldings. The relative solution viscosity of the mouldings was 1.193.

(b) In comparison, the same polycarbonate, but without the addition of azodicarbonamide, was injected into mouldings under the same conditions, and a relative solution viscosity of 1.286 was obtained.

The molecular weight reduction which was caused by the blowing agent and characterised by the reduction in the relative solution viscosity from 1.286 (b) to 1.193 (a) is accompanied by a reduction in strength.

The impact strength according to DIN 53 453 of the mouldings according to (a) is below 100 kJ/m$^2$, while the moulding according to (b) does not break in the impact test according to DIN 53 453.

The decrease in the relative solution viscosity and in the strength show that blowing agents having free $NH_2$—groups decompose hydrolysable plastics.

Oxalic acid-bis-hydrazide was spun onto the polycarbonate of Example 6 in the concentration indicated in Table 1. The mixture was compounded by extrusion at 240° C. The resulting granulate was injected at 300° C. into standard small rods having dimensions of 60 mm×6 mm×4 mm. The following relative viscosities were measured on the granulated material, as well as on the test bodies:

| Addition of oxalic acid-bis-hydrazide | relative solution viscosities | |
|---|---|---|
| | in the granulated material | in the test body |
| without addition (comparison) | 1.286 | 1.275 |
| 0.5 %, by weight | 1.257 | 1.188 |
| 0.75 %, by weight | 1.228 | 1.154 |
| 1.0 %, by weight | 1.212 | 1.129 |

Oxalic acid-bis-hydrazide obviously leads to a pronounced reduction of the molecular weight and to a deterioration in the mechanical properties.

TABLE 2

| Example | Structure | m.p. (°C.) | Processing parameters | | rel. solution viscosity |
|---|---|---|---|---|---|
| | | | Cylinder temperature | Cooling time | |
| 8 | C$_6$H$_5$—SO$_2$—NH—N=CH—C$_6$H$_{11}$ | 153 | 240/350/350/350° C. | 60 sec | 1.226 |
| 9 | C$_6$H$_5$—SO$_2$—NH—N=C(CH$_3$)—C$_6$H$_5$ | 131 | 250/310/330/330° C. | 60 sec | 1.264 |
| 10 | C$_6$H$_5$—SO$_2$—NH—N=C(CH$_2$CH$_3$)$_2$ | | 240/260/280/280° C. | 45 sec | 1.246 |
| 11 | C$_6$H$_5$—SO$_2$—NH—N=(tetrahydronaphthyl) | 192 | 260/330/350/350° C. | 60 sec | 1.251 |

TABLE 2-continued

| Example | | m.p. (°C.) | Processing parameters | | rel. solution viscosity |
|---|---|---|---|---|---|
| | | | Cylinder temperature | Cooling time | |
| 12 | ⟨phenyl⟩—SO₂—NH—N=C(CH₃)—CH₂—CH₂—COOH | 240/280/310/-310° C. | 45 sec | 1.234 | |

The following Examples according to the present invention show that blowing agents based on hydrazones in which there is no basic amine group, do not exert an appreciable influence on the molecular weight.

The monosulphohydrazones indicated in Table 2 were deposited individually onto the polycarbonate of Example 6 in a tumbler in an amount of 0.35% by weight based on polycarbonates, so that the blowing agent was distributed evenly over the surface of the individual granules.

The granulated material coated with blowing agent was injected on a Mannesmann-Demag DNC II 80 injection moulding machine into rectangular plates having dimensions of 150 mm×90 mm×8 mm and a volume weight of 0.9 g/cm³.

Parameters of the machine (shut-off nozzle, screw speed 18 r.p.m.; injection pressure 127 bars maximum); dwell pressure: 30 bars; dynamic pressure: 15 bars; pause time: 3 secs; temperature of mould: 50° C. The cylinder temperatures required for an optimum foam production depend on the blowing agent, and they are listed in Table 2. All the products may be processed into polycarbonate mouldings, since when the process was carried out without a nucleation auxiliary, the foam was coarsely porous.

The reduction in molecular weight, characterised by the decrease in the relative solution viscosity of 1.290 in the starting granulated material was only influenced to a slight extent, the aromatic sulphonyl hydrazones in particular having very little influence on the reduction in molecular weight.

Example 13

A polycarbonate having an identical melt viscosity to the one in Example 6 and containing 5%, by weight, of glass fibres (volume weight 1.240) was mixed with 0.3%, by weight, of the compound:

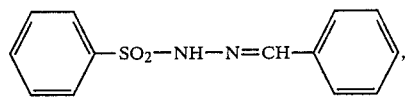

m.p. 112° C., gas yield at 260° C., 90 ml/g by spinning in an asymmetric moved mixer.

The mixture was foamed as in Examples 7 to 12, but with 240/300/320/320/320 (nozzle) °C. as the cylinder temperatures to produce finely cellular, light-coloured round discs having dimensions of 200 mm×8 mm and having a density of 0.9 g/cm³.

The relative solution viscosity for the injection moulding was 1.282 and was 1.295 for the granulated material, which corresponds to a reduction of only 0.013 units. The impact strength of the foamed part according to DIN 53 453 and 37.1 kJ/m².

TABLE 2

| Example No. | Blowing agent | rel. solution viscosity | Impact Strength | |
|---|---|---|---|---|
| | | | acc. to DIN 53453 | in the falling ball test Wf Max |
| 14 | ⟨phenyl with two SO₂—NH—N=CH—phenyl groups (meta)⟩ | 1.273 | 32.8 kJ/m² | 68.9 J |
| 15 | ⟨phenyl—SO₂—NH—N=CH—phenyl, —O— linking two such units para⟩ | 1.285 | 34.1 kJ/m² | 88.1 J |

TABLE 2-continued
| Example No. | Blowing agent | rel. solution viscosity | Impact Strength acc. to DIN 53453 | in the falling ball test Wf Max |
|---|---|---|---|---|
| 16 | 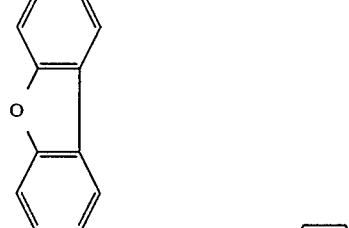 | 1.274 | 33.1 kJ/m² | 76.7 J |
| 17 | 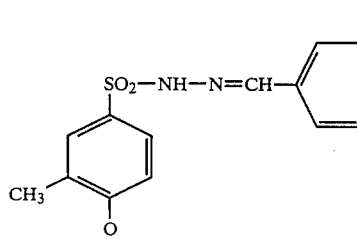 | 1.274 | 30.5 kJ/m² | 85.4 J |
| 18 | 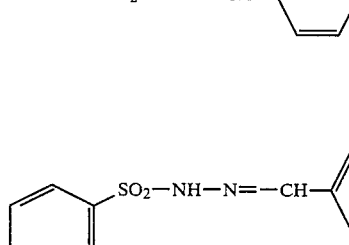 | 1.283 | 34.7 kJ/m² | 92.4 J |

TABLE 3

| Example | Blowing agent | rel. solution viscosity | Impact Strength acc. to DIN 53453 | in the falling ball test Wf Max |
|---|---|---|---|---|
| 16 | (structure shown below) | 1.274 | 33.1 kJ/m² | 76.7 J |
| 17 | (structure shown below) | 1.274 | 30.5 kJ/m² | 85.4 J |
| 18 | (structure shown below) | 1.283 | 34.7 kJ/m² | 92.4 J |

The bis-sulphonyl hydrazones indicated in Table 3 were introduced into an asymmetric moved mixer onto the polycarbonate containing 5% of glass fibres of Example 13. The plastics/blowing agent mixtures were processed into mouldings, as described in Example 9, at cylinder temperatures of 240/280/330/330° C. (nozzle). In every case, light-coloured, finely-cellular integral foam mouldings were produced having the properties stated in Table 3.

We claim:

1. A process for the production of a cellular polymer which comprises using as a blowing agent an arylsulphonyl hydrazone corresponding to the following general formula:

$$Ar(SO_2-NH-N=R)_x \qquad (I)$$

wherein
Ar represents a benzene, naphthalene, diphenyl, diphenyl ether, diphenyl sulphone or diphenylene oxide radical which may be substituted one or more times by methyl and/or chlorine;
R represents the residue of an aldehyde or ketone without the carbonyl oxygen atom; and
x represents 1 or 2.

2. A process as claimed in claim 1 wherein N,N'-bis-benzylidene-diphenyl sulphone-3,3'-disulphonylhydrazine is used.

3. A process as claimed in claim 1 or claim 2 wherein the polymer is a polycarbonate or a polybutylene terephthalate.

4. N,N'-bis-benzylidene-diphenyl sulphone-3,3'-disulphonylhydrazine.

* * * * *